July 5, 1955
J. D. BROWNELL
Plant Pat. 1,404
ROSE PLANT
Filed Oct. 5, 1954
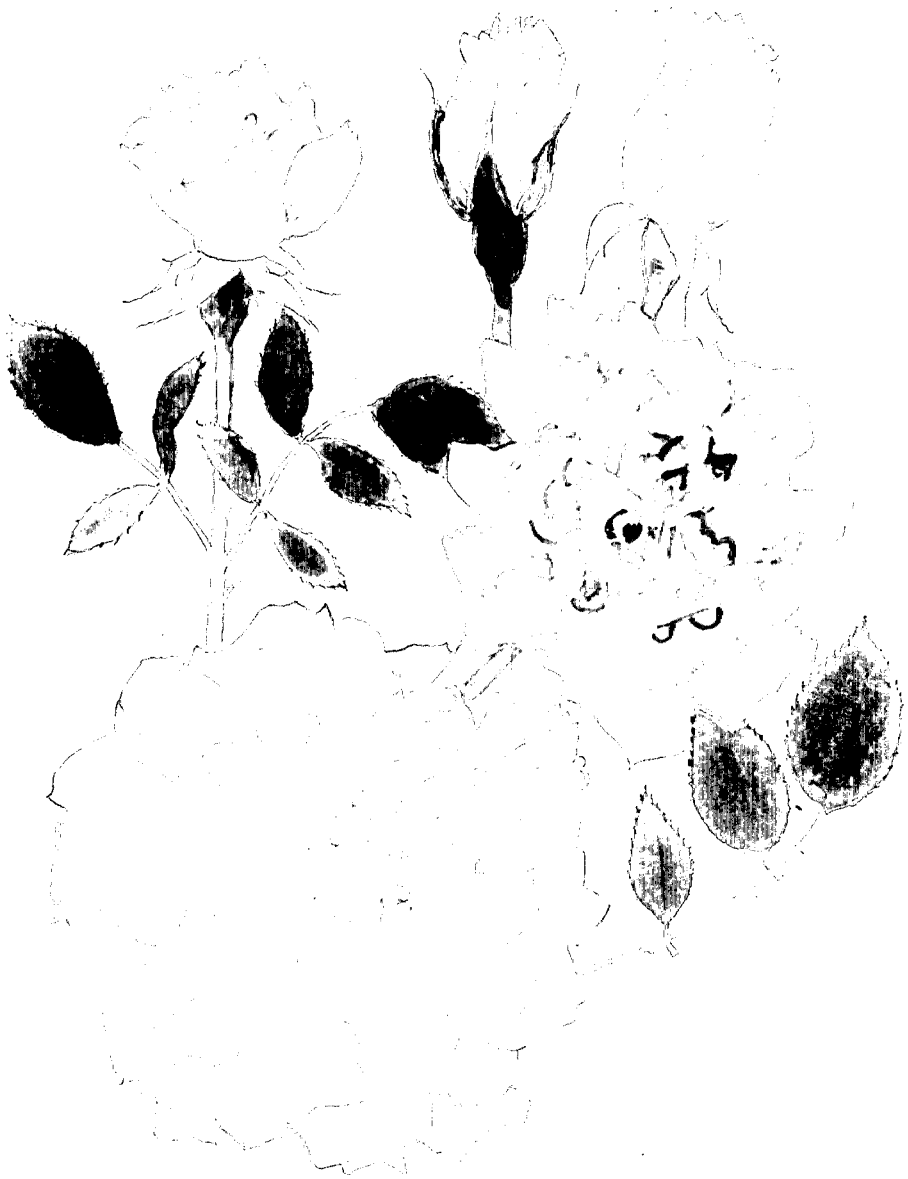
Josephine D. Brownell.
INVENTOR.

United States Patent Office

Plant Pat. 1,404

Patented July 5, 1955

1,404

ROSE PLANT

Josephine D. Brownell, Little Compton, R. I.

Application October 5, 1954, Serial No. 460,524

1 Claim. (Cl. 47—61)

My invention relates to roses and especially to a new, original and distinct variety of rose plant of the class known commercially as "hybrid teas" and is a variant in that class, being a *Rosa wichuraiana* hybrid tea hybrid, produced by me and under my direction in the breeding grounds of my research gardens in Little Compton, Rhode Island, by selection of variety variations and by cross pollenation, which can be and has been asexually reproduced.

My new rose plant is new as to the following characteristics and especially as to their joint association with the characteristics inherited from *Rosa wichuraiana*, of hardiness, or immunity from serious injury on account of cold temperatures prevailing in certain parts of the northern United States;

The deep red color (ordinary dictionary definition) of its petals, in combination with the unique brilliance thereof and their tendency to hold these colors under exposure;

The novelty and variation within certain definite limits of the form of the bloom, its character of holding its informal arrangement for a long time and the petallage of the flowers;

Its character of fragrance;

Its unusual abundance of flowers, notable after early bloom time and until frost;

The intensity of its remontant and everblooming or reblooming character.

Its character of ascending very little in height and notably spreading in width by recurrent branching and progressively longer stems from the base.

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by blackspot, under certain definite conditions of exposure, without any cultural control.

In the acompanying drawing forming a part of this specification I have shown my new rose in its natural colors, that is, as near as is possible to do so artificially.

My new rose is otherwise described as follows:

ESSENTIAL INFORMATION

*Type*

Hybrid tea, *Rosa wichuraiana* hybrid, notably dwarf, and spreading, for garden display, cut flower and forcing or growing under glass.

*Class*

Hybrid tea crossed with *Rosa wichuraiana*, further restricted by originator to include only those varieties that can survive moderately low sub-zero temperatures.

*Breeding*

This variety was produced and bred by me and under my direction by propagation, selection and cross pollenation.

It came into being as a seedling grown from a seed born on a plant of Queen o' the Lakes, Plant Patent No. 1,003, and the pollen parent was an unnamed seedling.

The pollenation that fertilized the seed that grew into my new rose, as well as the two previous pollenations that produced its two parents, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 8, 1949.[1] The seed was planted for me and under my direction on December 22, 1949, and the date of the first flower was July 31, 1950.

The plant and flower seemed to me to be of unusual merit and I have since made and directed extensive propagations and tests thereof.

Plants of this variety budded from this seedling on to *Rosa multiflora* root stocks, have after being exposed to moderate subzero temperatures, survived and bloomed normally the following season in the hybrid tea manner. The variety has been propagated by budding at Little Compton, Rhode Island, in the months of July and August 1950 and 1951 and the characters have successively reproduced, true to the original seedling.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three and occasionally more on each stem, in the usual hybrid tea type of cluster. And frequently on unsually large stems in open clusters in the manner of Florabundas, or more free flowering types; and later in the season branches frequently grow therefrom with terminal flowers.

All of the foregoing bloom expression usually obtains the first year after budding, on maidens and on two year old plants the first growing season after being transplanted.

The pedicels and peduncles are medium in diameter and medium in length, erect, stiff, almost smooth, free from large prickles, and bristles. Stems are medium short, diameter medium and notably stiff and rigid.

*Quantity of bloom*

Free, being cumulative in quantity from year to year as the plant increases in size, flowering through the summer and fall.

*Fragrance*

Distinctive, pleasing China tea in combination with that of *Rosa wichuraiana*, under favorable environment.

*Bud*

Neck normal as described, opens well, being little to not at all affected by hot or wet weather or both, as to color and form, except at very high temperatures the color is less intense and the form of the petals is less recurled.

Before the calyx breaks the size is medium, form moderately high pointed, the sepals are usually normal and regular, tapering to lanceolate at their apex, rarely with one only, foliaceous appendage, rarely with a spur on either side thereof, turning back and usually downward as the bud opens, usually no other spurs on sides.

[1] This and other dates herein are approximate.

Color of the bud as calyx opens, outside Cardinal Red at 822/3; color reference to English Horticultural Color Chart.[2]

*Bloom*

Outer petals irregularly recurled under normal environment.

Color outside of petals, outer rows colored as stated; inner petals, outer side, same shading to Cardinal Red at 822/1. Inner side of petals, Currant Red at 821.

Color softens slowly to nearly Crimson at 22/1.

Color slightly variable dependent upon quality of sun or other light.

The flower usually varies in size between 3½ to 4 inches in diameter when fully open, petals average between 50 and 60, frequently some smaller petals and petaloids in the center, variable in number.

The flower opens moderately ovate and medium high centered, informal, with delayed display of stamens and pistils. The petals are variable from obovate to ovate to irregular and informal as to arrangement and recurl, and edges of the smaller petals occasionally notably irregular. Texture is medium to thick; both sides brilliant. The time of opening in favorable conditions is about four days.

The petals are substantial and after about six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Productive organs*

Stamens, quantity variable, medium short of slightly uneven length.

Anthers, nearly Nasturtium Red at 14/2. Filaments, nearly Tangerine Orange at 9/3.

Pistils are several of nearly even length, averaging from one-half inch to one-third inch long.

Sepals are persistent and break off easily.

PLANT

*Foliage*

Is abundant, of compound leaves of three to five leaflets near the flower, five leaflets lower down the stem and occasionally seven leaflets in the middle of the stems and nearer the base. Often with short narrow leafy formations variously positioned near the flower. Size of leaflets notably small. Form of leaflets usually nearly ovate with apex moderately acute, base rounded to slightly pointed, margins with slightly irregular small pointed serrations, petiolules medium short, and with slightly wider space than usual between leaflets.

The leaflets average in width about one-half of their length.

[2] Color references to same unless otherwise indicated.

Color of leaflets on the upper surface is slightly variable from Spinach Green at o960, irregularly shaded with Parsley Green at oo962, with reverse side nearly Asphodel Green, the last color reference is to Robert Ridgway Color Standards.

The rachises are moderately narrow to slender, upper side smooth except some very short hairs almost microscopic on edges. Under side moderately smooth, usually three to five short prickles.

Stipules are long, averaging about ⅞ inch long or a little less, notably narrow with sharp point, the upper edges of which normally form an angle of about 80 degrees.

Plant habit, dwarf, becoming spreading and low for a hybrid tea; heighth under favorable conditions up to two feet, by stems from the base and by rebranching and growth and enlargement and extension of the stems from the base. The growth is moderately free at first, developing more rapidly after one or two years under favorable vegetative opportunity.

Color of mature stems is Scheele's Green at 860/3, shading variously to nearly Parsley Green at oo962/2.

Prickles, several, frequently two to four between leaves, averaging in length about one-quarter inch, shading from Carmine at 21/2 to lighter at the base, turning lighter throughout and later to nearly colorless.

*Winter resistance*

A notable characteristic of this new rose is the resistance to moderate sub-zero temperatures in combination with its hybrid tea character, and its *Rosa wichuraiana* ancestry. The word temperature herein refers to the Fahrenheit scale.

*Comparisons*

This rose variety is one of a new race or type of rose, not found in nature or in commerce, produced by combining and by breeding several varieties containing different variations of expression, and using such resultant material as breeders.

The variety most nearly resembling my new rose is Handsom Red, Plant Patent No. 1,182, which lacks the dwarfness of my new rose; it grows two to three times as tall, the flowers average 50% larger and the leaflets are about twice as large.

My new rose is more branching, is of the polyanthus type, and could be classed in the class known commercially as Floribundas.

I claim:

A new and distinct variety of roseplant, substantially as shown and described characterized by its color, fragrance, form and color and its Wichuraiana traits.

No references cited.